United States Patent
Lo

(10) Patent No.: US 11,519,413 B2
(45) Date of Patent: Dec. 6, 2022

(54) OPTIMIZING PUMPING OF VARIABLE VISCOSITIES VIA MICROTEXTURED MINIATURIZED TESLA PUMP

(71) Applicant: THE REGENTS OF THE UNIVERSITY OF MICHIGAN, Ann Arbor, MI (US)

(72) Inventor: Joe Fu-Jiou Lo, Westland, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/285,164

(22) PCT Filed: Oct. 14, 2019

(86) PCT No.: PCT/US2019/056053
§ 371 (c)(1),
(2) Date: Apr. 14, 2021

(87) PCT Pub. No.: WO2020/081422
PCT Pub. Date: Apr. 23, 2020

(65) Prior Publication Data
US 2021/0363997 A1 Nov. 25, 2021

Related U.S. Application Data

(60) Provisional application No. 62/745,639, filed on Oct. 15, 2018.

(51) Int. Cl.
*F04D 7/04* (2006.01)
*F04D 1/00* (2006.01)
(Continued)

(52) U.S. Cl.
CPC ............ *F04D 7/04* (2013.01); *A61M 60/113* (2021.01); *A61M 60/216* (2021.01);
(Continued)

(58) Field of Classification Search
CPC . F04D 7/04; F04D 1/00; F04D 13/024; F04D 29/22; F04D 29/426
See application file for complete search history.

(56) References Cited

U.S. PATENT DOCUMENTS 5,297,926 A * 3/1994 Negishi ................. F04D 29/681
415/206
6,135,708 A * 10/2000 Conrad ................. F04D 17/161
415/182.1
(Continued)

FOREIGN PATENT DOCUMENTS

| EP | 2975214 A1 | 1/2016 |
| EP | 3104014 A1 | 12/2016 |
| RU | 2631854 C1 | 9/2017 |

OTHER PUBLICATIONS

International Search Report and Written Opinin of the International Searching Authority issued in PCT/US2019/056053, dated Dec. 12, 2019; ISA/US.
(Continued)

*Primary Examiner* — Eldon T Brockman
(74) *Attorney, Agent, or Firm* — Harness, Dickey & Pierce, P.L.C.

(57) ABSTRACT

An integrated flow source is a limiting factor in numerous microfluidic applications. In addition to precise gradients and controlling molecular transports, a built-in source of stable and accurate flow can enable novel shear stress modulations for long-term cell culturing studies. The Tesla turbine, when used as a pump on the microfluidic regime, produces stable and accurate fluid gradients by utilizing laminar flow between its rotating discs Utilizing a stereolithography based 3D printer, a tesla pump (Ø10 cm) and associated housing capable of driving a microfluidic gradient is provided having a printed rotor surface topology of the pump in order to enhance pumping of biological fluids like
(Continued)

blood at elevated viscosities. The surface topology is tuned via 3D pixilation, and this modulation completely recovered the pressure loss between pumping water at 1 cP versus glycerol solution at 3 cP. As a result, increased fluid viscosities, and even Non-Newtonian viscosities, can be used.

12 Claims, 13 Drawing Sheets

(51) Int. Cl.
    *F04D 13/02*     (2006.01)
    *F04D 29/22*     (2006.01)
    *F04D 29/42*     (2006.01)
    *A61M 60/216*    (2021.01)
    *A61M 60/419*    (2021.01)
    *A61M 60/37*     (2021.01)
    *A61M 60/113*    (2021.01)

(52) U.S. Cl.
    CPC .......... *A61M 60/37* (2021.01); *A61M 60/419* (2021.01); *F04D 1/00* (2013.01); *F04D 13/024* (2013.01); *F04D 29/22* (2013.01); *F04D 29/426* (2013.01)

(56) References Cited

U.S. PATENT DOCUMENTS

| | | |
|---|---|---|
| 10,790,723 B2 * | 9/2020 | Irvin, Sr. ................ B01D 45/12 |
| 2005/0180845 A1 | 8/2005 | Vreeke et al. |
| 2007/0059156 A1 | 3/2007 | Blanchard et al. |
| 2017/0051757 A1 | 2/2017 | Sarmiento |

OTHER PUBLICATIONS

Extended European Search Report regarding Patent Application No. 198731119, dated Jun. 14, 2022.

* cited by examiner

| Print Angle | RMS Topology | S.D. |
|---|---|---|
| 0° | 3.01 μm | 0.65 |
| 22° | 3.13 μm | 0.70 |
| 45° | 3.30 μm | 0.63 |

OPTIMIZING PUMPING OF VARIABLE VISCOSITIES VIA MICROTEXTURED MINIATURIZED TESLA PUMP

CROSS-REFERENCE TO RELATED APPLICATIONS

This application is the U.S. National Phase Application under 35 U.S.C. 371 of International Application No. PCT/US2019/056053 filed on Oct. 14, 2019, which claims the benefit of U.S. Provisional Application No. 62/745,639, filed on Oct. 15, 2018. The entire disclosures of the above applications are incorporated herein by reference.

FIELD

The present disclosure relates to tesla pumps and, more particularly, relates to methods and systems for optimizing microfluidic pumping of variable viscosities using a miniaturized tesla pump (µ Tesla).

BACKGROUND AND SUMMARY

This section provides background information related to the present disclosure which is not necessarily prior art. This section also provides a general summary of the disclosure, and is not a comprehensive disclosure of its full scope or all of its features.

Pumping of biological fluids has remained relatively unchanged in the second half of the 20th century. Pumping is central in a wide range of biomedical applications, including intravenous (IV) infusions, blood transfusions, biofiltration, and hemodialysis machines. However, these technologies often suffer from a number of disadvantages, as outline in Table 1 below.

| Procedures | Flow Technologies | Issues |
| --- | --- | --- |
| IV infusion | gravity | Unstable flow, embolism |
| Drug infusion | Syringe pumps | Volume limits, pressure |
| Filtration (e.g. hemodialysis) | Peristaltic pumps | Pulsatile, shear [1] |
| Blood transfusion | Peristaltic pumps | Pulsatile, shear |
| Heart assist pumps (LVAD) | Screw/diaphragm pump | Shear, reliability [2, 3] |

In these applications, either gravity, bladed rotors, or more commonly, the peristaltic squeezing of tubing provided the main source of flow pressure. However, pumping using these pressure sources incurs shear damage to cellular components in blood, e.g. drops in hematocrit, erythropoietin, and increases in hemolysis due to sharp pressure gradients and time varying flow velocities.

Current strategies attempting to overcome these issues rely on heparin coating on components and systemic injections in patients, especially for hemodialysis sessions. The latter strategy minimizes blood clots from cellular damages, but introduces significant risks of low blood pressure in patients and associated side effects. Moreover, by employing pharmaceutical solutions, e.g. heparin, to treat the symptoms rather than addressing the physical traumas to blood in extracorporeal flows, the technology of biofluidic pumping has stagnated.

Recent advance in biofluidic pumping has been made from the field of microfluidics to control flows ranging from mL to µL and nL/min domain. Novel integrated microfluidic pumps include acoustofluidic pumps and inkjet print heads; electroosmotic pumps; electrolysis gas pressure pumps; capillary force siphoning, a la paper microfluidics; and valve-based peristaltic pumps and commercial miniaturized insulin pumps (STMicroelectronics, NV). However, aforementioned microfluidic pumps cannot provide smooth laminar flow due to their pulsatile driving forces of valves and acoustics, or require applied voltages that render them incompatible with blood flows.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 11A:
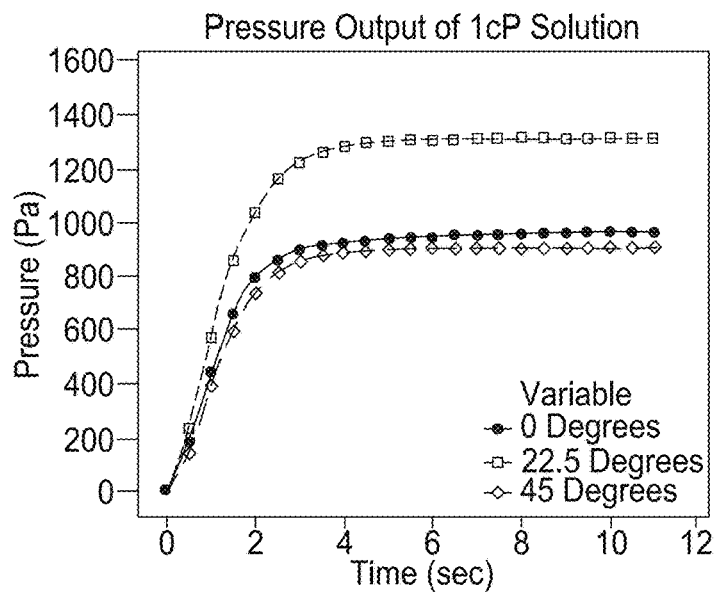
Figure 11B:
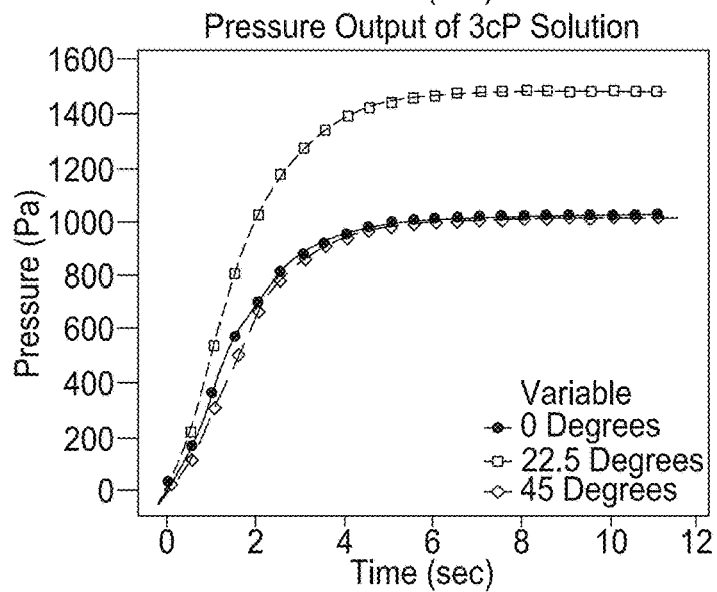
Figure 11C:
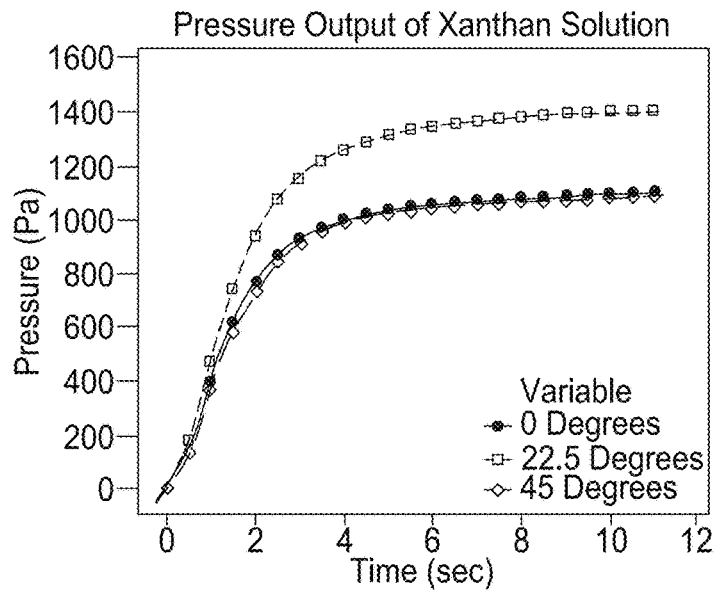

FIGS. 11A, 11B, and 11C illustrate the transient pressure outputs of water, glycerol, Xanthan solutions, respectively.

Figure 11D:
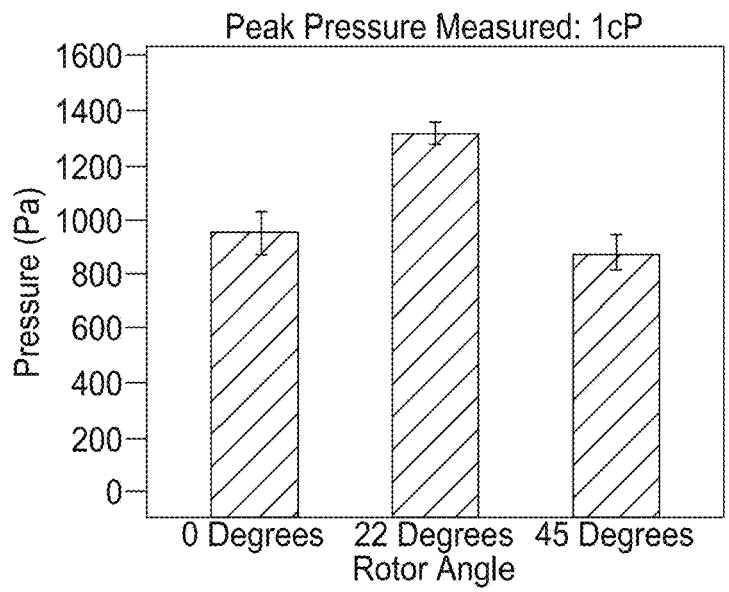
Figure 11E:
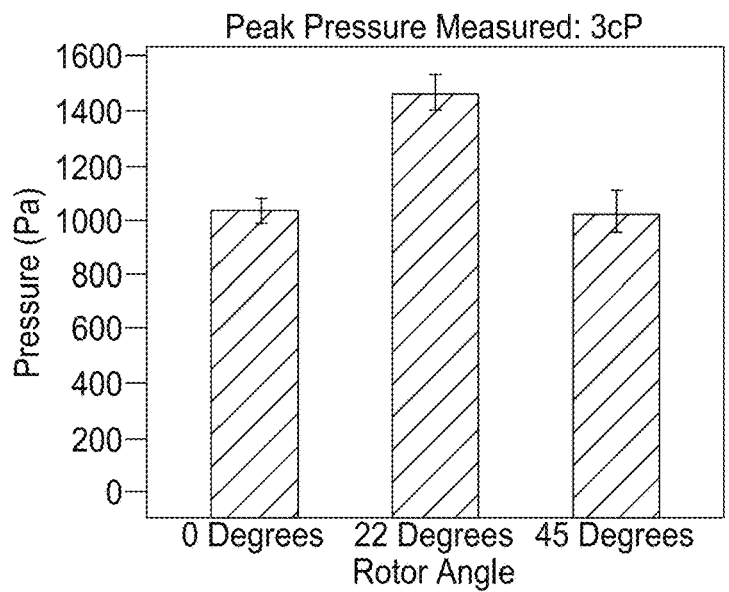
Figure 11F:
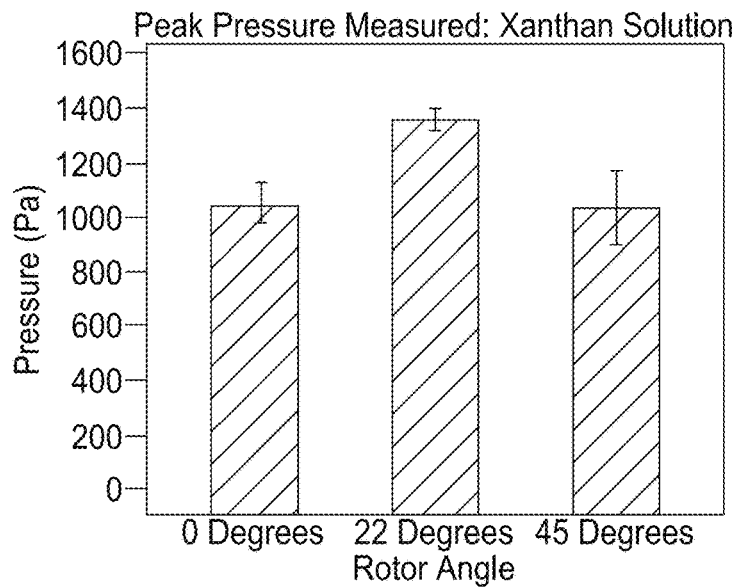

FIGS. 11D, 11E, and 11F illustrate the peak pressure outputs of water, glycerol, Xanthan solutions, respectively.

Figure 12C:
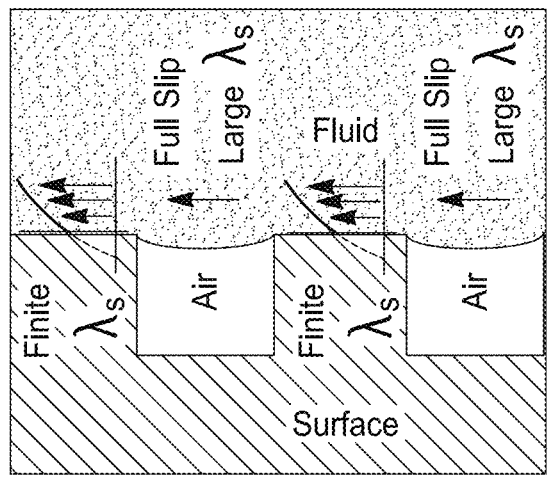
Figure 12B:
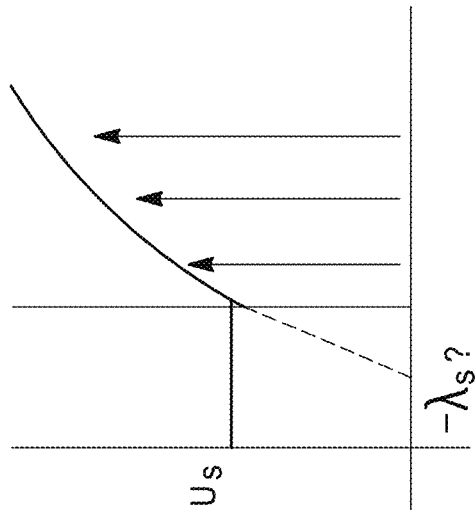
Figure 12A:
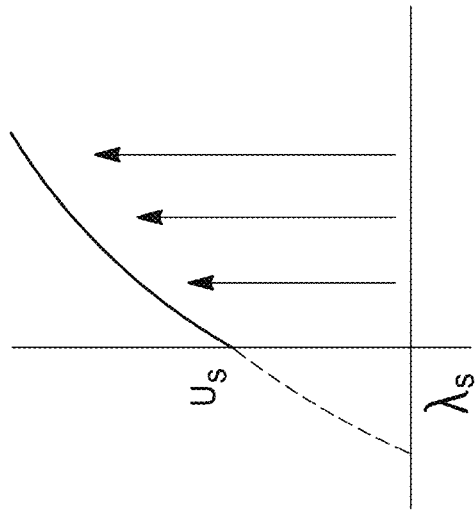

FIG. 12A illustrates a standard slip.

FIG. 12B illustrates a textured surface slip.

FIG. 12C illustrates a super hydrophobic slip according to conventional design.

Figure 13A:
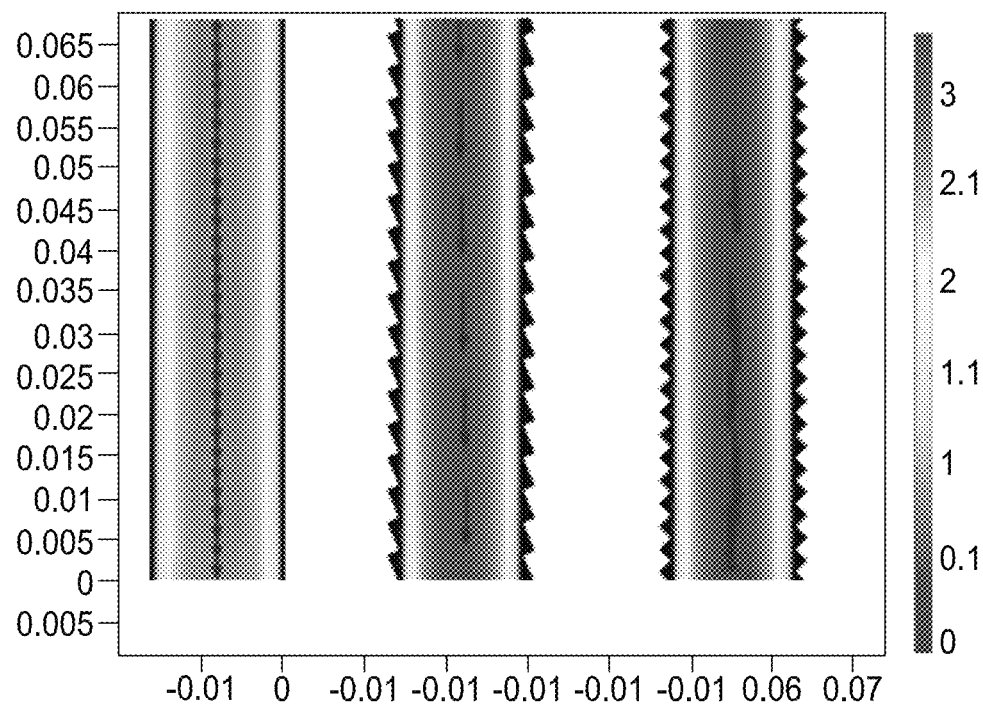

FIG. 13A illustrates a model with assumed no-slip conditions and measured pressure outputs of pumping water with μTesla rotors having fluid flow with textured channel walls to simulate μTesla tuning with 0°, 22°, and 45° print geometries.

Figure 13B:
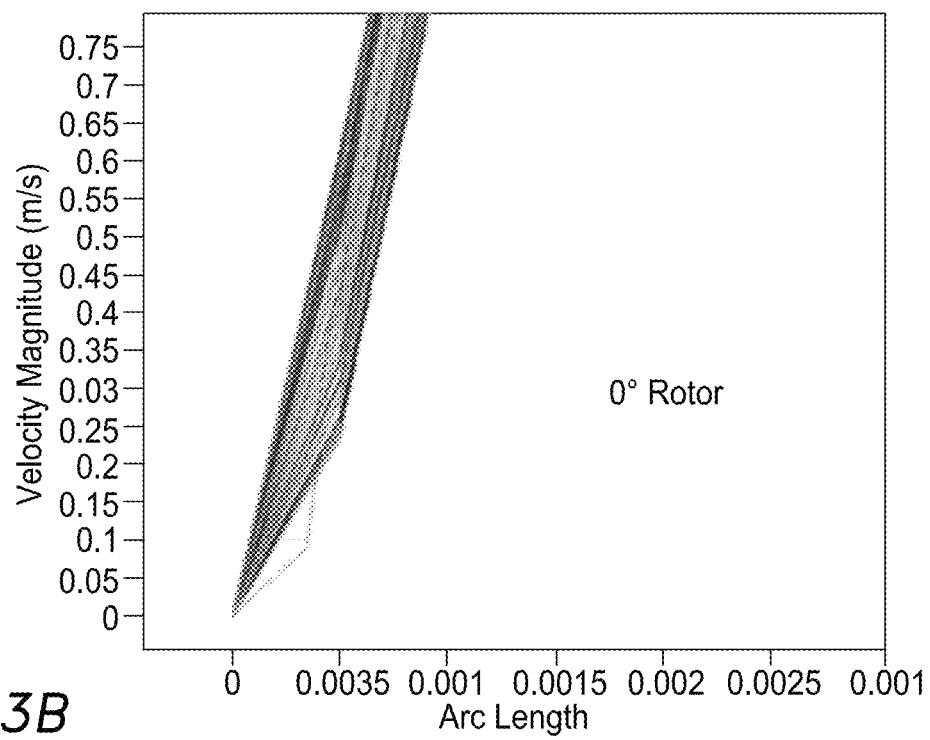

FIG. 13B illustrates a zero degree (0°) print version with no-slip boundary as dictated by model.

Figure 13C:
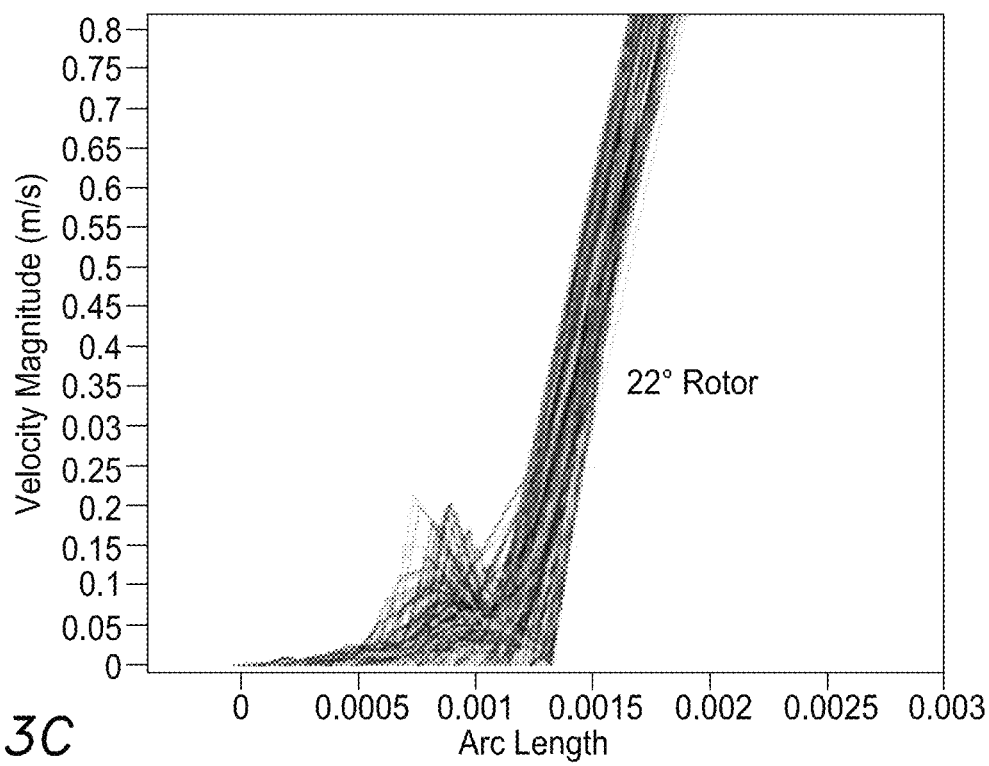

FIG. 13C illustrates a 22° print version that pushes the velocity profile out towards the center of the channels (i.e. toward the right).

Figure 13D:
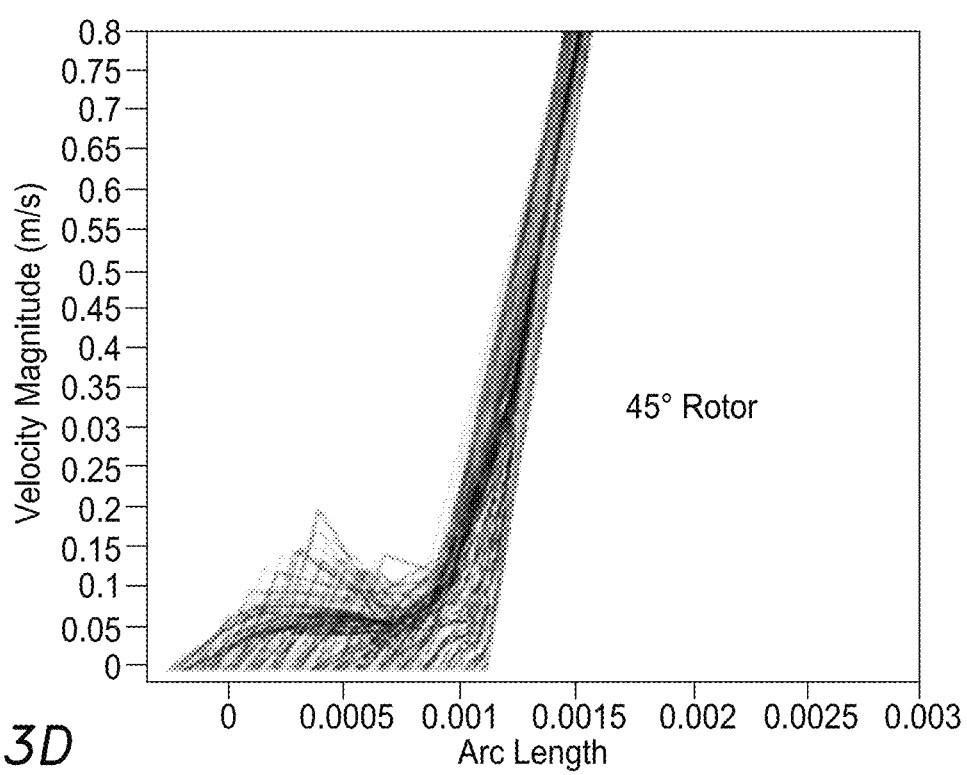

FIG. 13D illustrates a 45° rotor that does not push the profile out as far as the 22° rotor of FIG. 13C.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
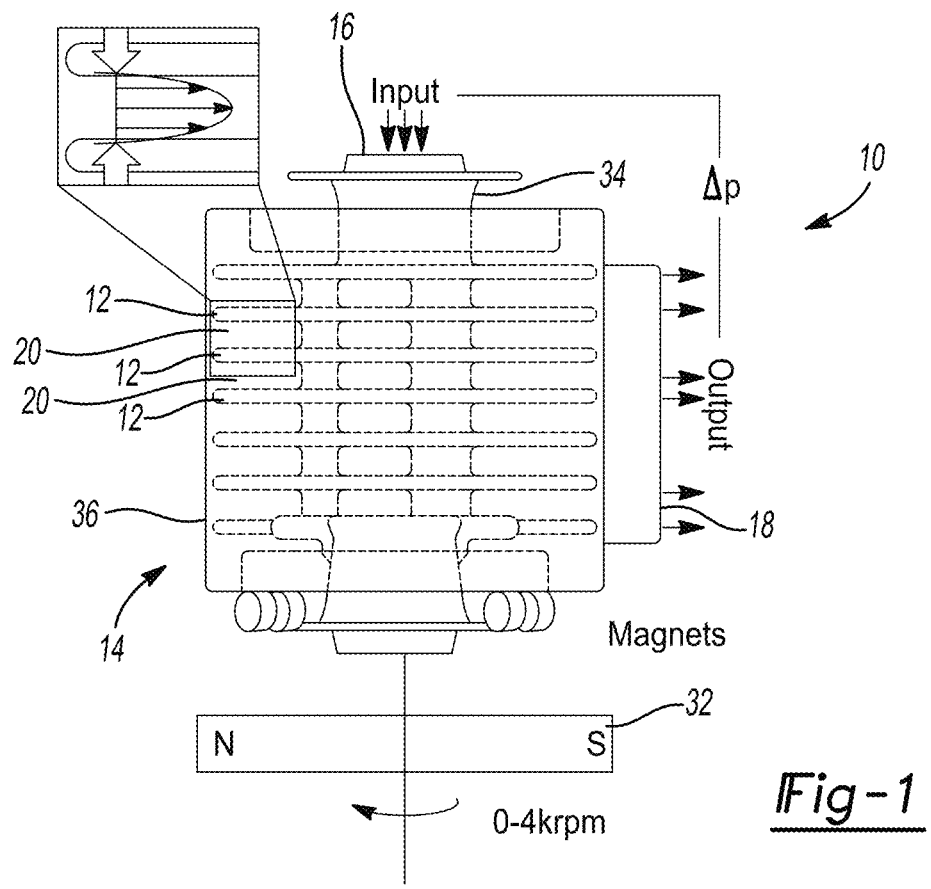
FIG. 1 illustrates a side view of a µTesla pump according to the principles of the present teachings.

According to the principles of the present teachings, as illustrated in FIGS. 1-7 and particularly FIG. 1, in some embodiments, a miniaturized, magnetically-coupled Tesla pump 10 (also referred to as μTesla pump) is provided having advantageous construction and method of operation that leverages low Reynolds number laminar flows between rotating disks 12 to generate pressure. Fluid enters the rotor assembly 14 axially at an input 16 and is spirally propelled by no-slip boundary forces of laminar flow, thus building pressure continuously without oscillations. Flow with oscillating pressure creates a fluctuating range of fluid velocities with higher shear stress compared to flows with the same average flow rate. By eliminating this fluctuation, shear stress can be minimized to reduce mechanical damage to blood and hemolysis.

As illustrated in FIG. 1, μTesla rotor assembly 14 leverages laminar flow between circular disks 12 to generate velocity. The rotor assembly 14 is a multi-disk construction with axial input 16 flow and lateral output 18 flows during operation. Input 16 flow enters the gaps 20 between disk 12, whose rotation drags the fluid in a spiral towards the outer edges of the rotor assembly 14. This flow is optimal at microfluidic scale as more of the laminar velocity profile extends towards the surfaces of the rotating disks 12.

Boundary Layer Flow at the Surface of μTesla Rotors

Figure 2:
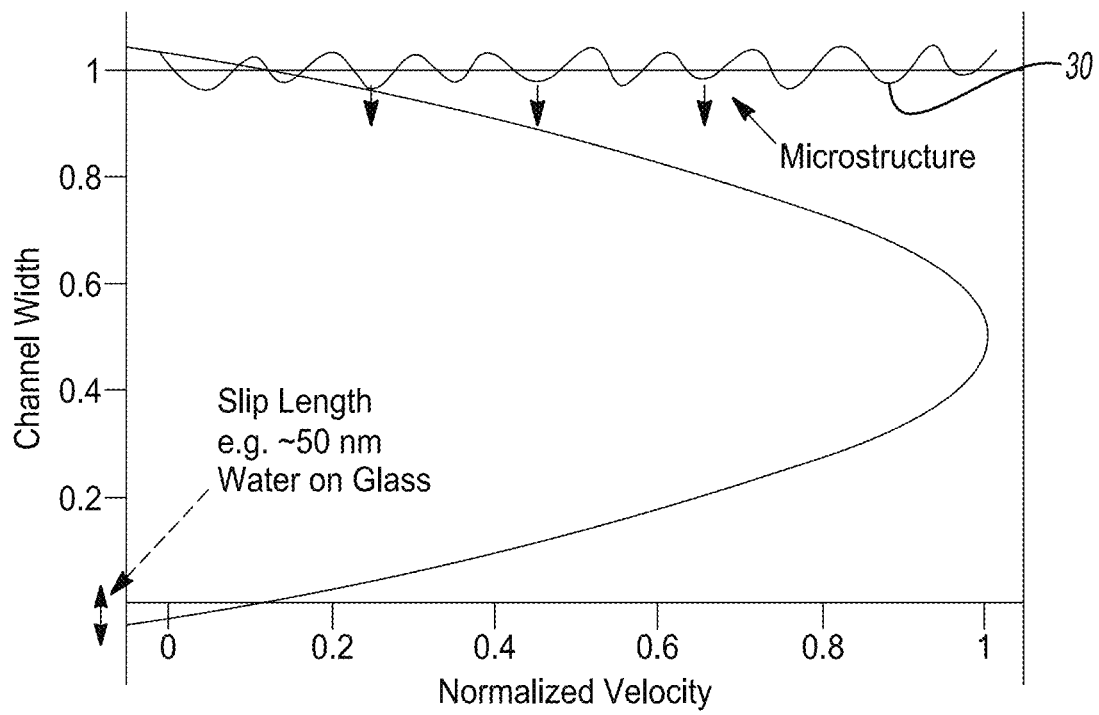
FIG. 2 illustrates a graph of normalized velocity for a channel width between disks of the µTesla pump.

Nikola Tesla patented the Tesla turbine for geothermal power generation in 1913 (see U.S. Pat. No. 1,061,206). However, current understanding of fluidic mechanics opens a new area for the optimization of Tesla rotors. The coupling of mechanical rotation into fluid velocity at the rotor disk surfaces relies on the no-slip boundary conditions assumed in laminar flows. This boundary condition is a direct result of the electrical double layers created to balance the electrostatic forces at the surface, where the layer below the slip plane remains stationary held on by surface forces. Technically, the no-slip condition is physically finite, and even the well-behaved water-glass interface deviates from no-slip with a slip length of about 50 nanometers, as illustrated in FIG. 2. Thus, the slip distance can be described for a particular fluid-surface interface, which dictates the momentum transfer in a Tesla rotor.

Normally, in conventional designs, the 50 nanometer electric double layer is inaccessible to the bulk of fluidic flow. However, in a micro/nanofluidic geometry, significant portion of the flow velocity profile will be extended into this double layer thickness. Furthermore, by designing microscaled structures 30 on the surface of the µTesla rotor assembly 14 and/or disks 12, the double layer can be extended further into the flow velocity profile, to leverage additional surface-fluid coupling. Beyond a certain extreme, these microstructures 30 will perturb the laminar flow profile, disturbing the aforementioned smooth surface-fluid coupling. Furthermore, microstructures 30 can push the boundary layer further inward of the velocity profile.

Surface Tuning to Optimize µTesla Pumping at Specific Viscosities

Figure 3:
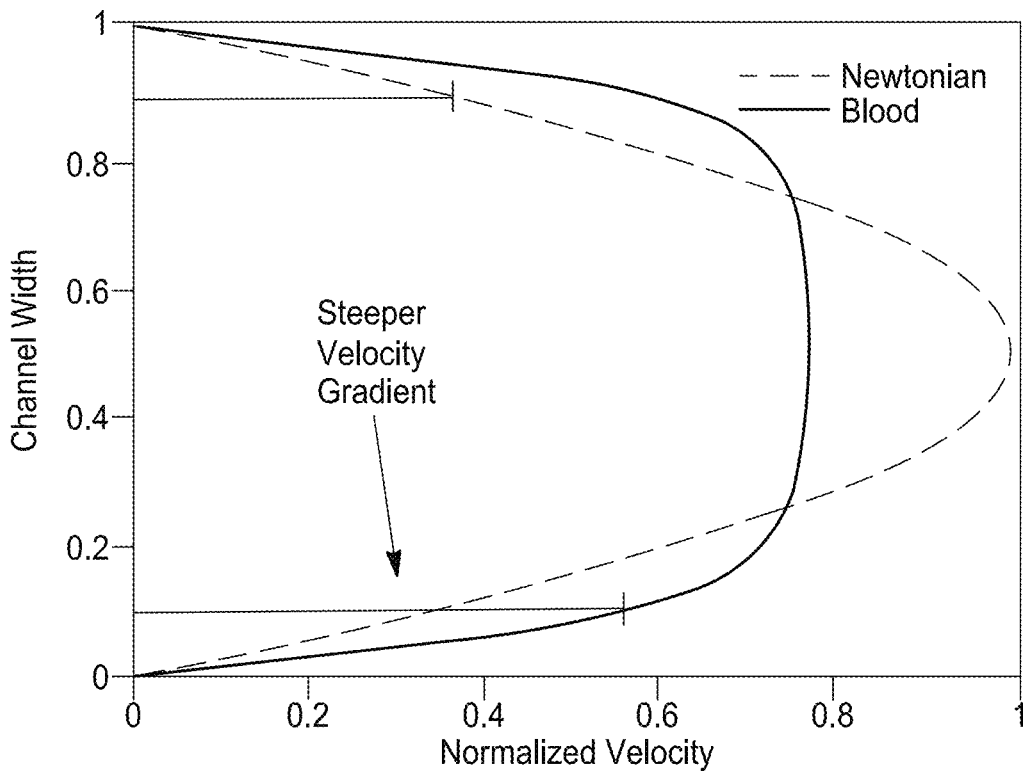
FIG. 3 illustrates a graph of normalized velocity for a channel width between disks for Newtonian fluids and blood normalized to yield the same average flow velocities.

In some embodiments, there exists an optimal surface microfeature or microstructure 30 that provides the best surface-fluid coupling for specific fluid viscosities. For Newtonian fluids, flow in the µTesla pump 10 will be laminar with a parabolic velocity profile that is inversely proportional to viscosity. This means Newtonian fluid with higher viscosities will have lower coupled velocities and pressures, e.g. harder to pump. However, biofluidics, such as blood, are non-Newtonian, where blood viscosity decreases with flow rate (shear rate) and becomes easier to pump. This also means that the non-Newtonian velocity profile becomes a flattened parabola, as illustrated in FIG. 3, with sharper velocity gradients extending towards the surface boundaries. By matching the size of surface microstructures 30 to these gradients, the no-slip boundary condition can be optimally coupled to create higher fluid velocities and pressures.

Moreover, greater coupling between the microstructures 30 on the surface of rotor disks 12 and the fluid will also change the transient pumping characteristics of µTesla pump 10. At the optimal coupling, faster pressure changes can be achieved for temporal modification of flow velocity or pressure. This transient characteristic can also be used as a quantitative measure, where faster transients denote greater couplings compared to non-structured surfaces.

With continued reference to FIG. 3, it can be seen that shear thinning flow results in a flattened velocity profile. Shear thinning in fluids like blood (red) reduces flow velocity at higher shear rate. This translates to sharper shoulders (steeper gradients) and a flattened velocity profile compared to the normal parabolic profile (blue) of laminar flows. Both flow profiles were normalized to yield the same average flow velocities.

Specific Surface Geometry for Tuning

Boundary layer flows as described earlier are limited to within 100 nm from the wall surfaces of the flow. Therefore, any surface modification should produce features greater than this dimensional scale. On the other hand, once feature's dimension approaches the development length of the flow (~100 µm for microfluidics), the laminar flow profile itself will be affected. To limit the effect of geometry for only fluid-surface coupling, in some embodiments, the optimal feature sizes should be limited to between 100 nm and 100 µm. More particularly, in some embodiments, the surface microstructures or features 30 can have vertical and lateral geometries that are within 3-50 µm in size in accordance with microfluidic flows.

Figure 4A:
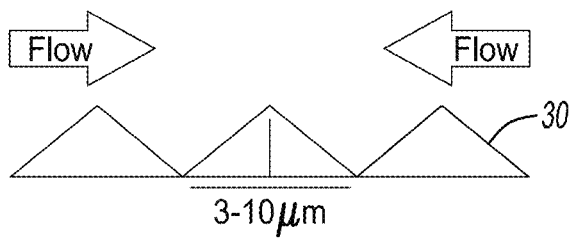
FIGS. 4A-4C illustrate side views of a plurality of microstructures upon a disk of the µTesla pump according to the principles of the present teachings.
Figure 4B:
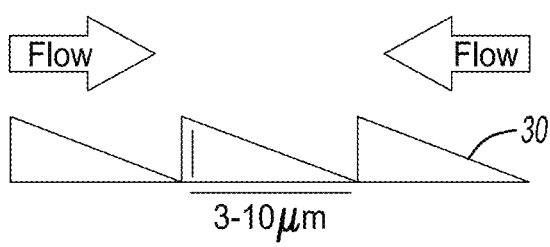
Figure 4C:
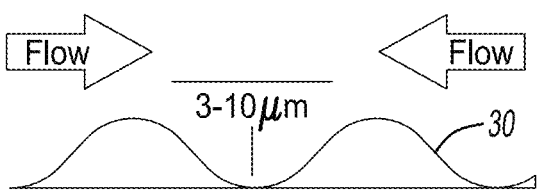

Furthermore, with particular reference to FIGS. 4A-4C, in some embodiments the type of surface microstructure or feature 30 can have either directional or symmetrical shapes. A symmetrical feature 30 could be designed for rotors that may need to be operated in both pumping and syphoning directions. For example, an equilateral triangle can be operated in both rotor directions (see FIG. 4A). On the other hand, a directional, saw-tooth shape would see more dramatic effects in one direction rather than another, for a more directional pumping (see FIG. 4B). Lastly, velocity profiles in flows to produce smooth transitions, which reduces the chances of flow disruptions and vortices thereby reducing rotor vibrations, may employ a sinusoidal geometry at the same size scale as a triangular geometry (see FIG. 4C), thereby providing the same effect on fluid-surface coupling with reduced vibrations and pressure fluctuations.

Figure 5A:
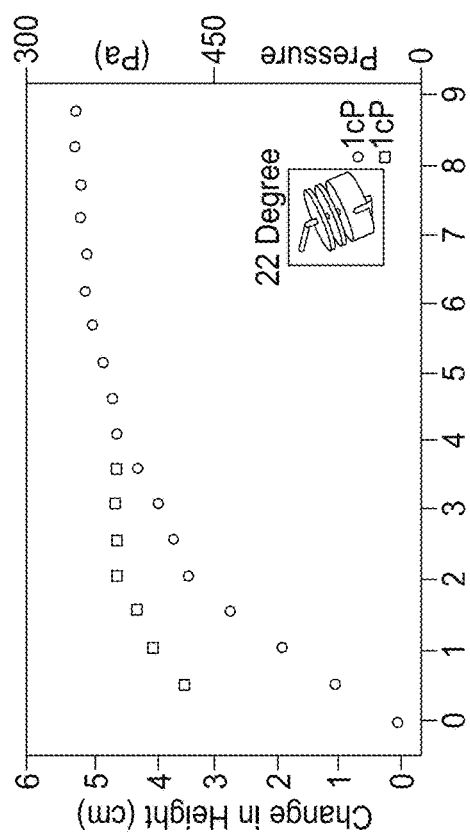
FIGS. 5A-5C illustrate graphs for pump pressure over time for 0 degree print, 22 degree print, and 45 degree print, respectively.
Figure 5B:
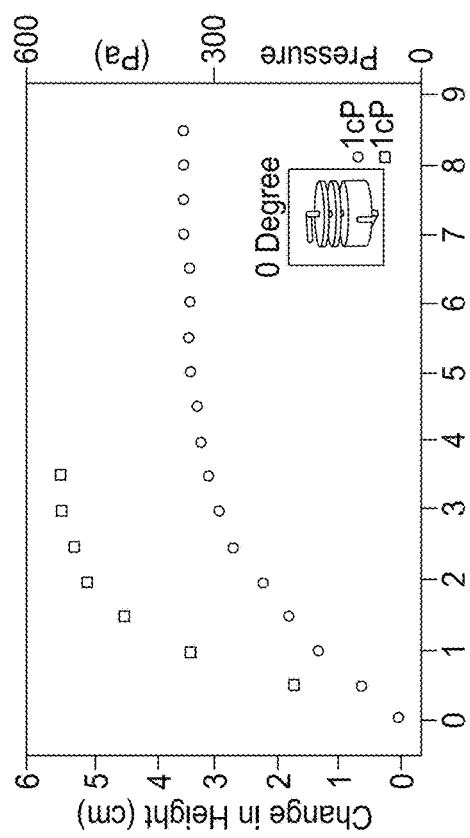
Figure 5C:
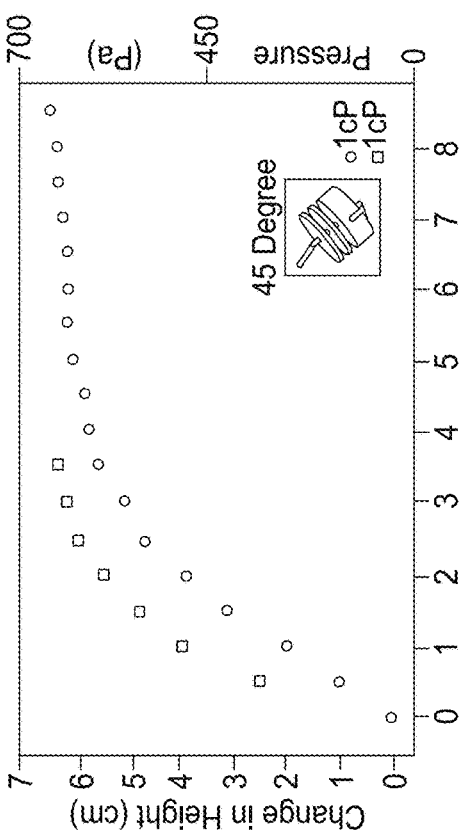
Figure 5D:
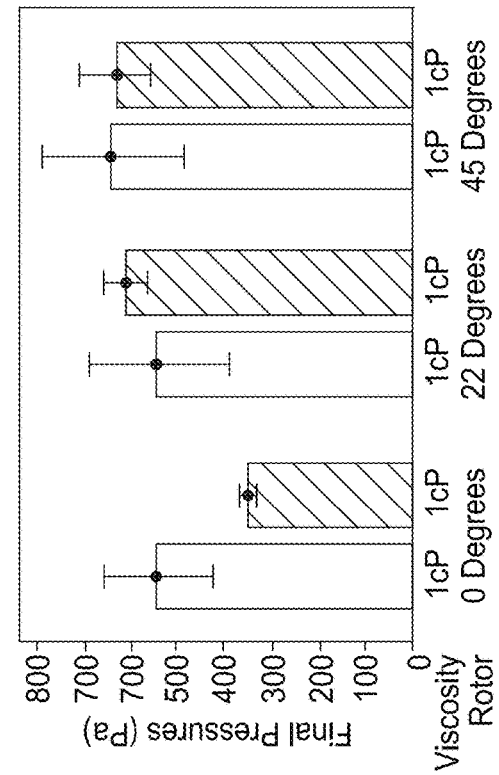
FIG. 5D illustrates a graph showing final hydrostatic pressure ($\rho g \Delta h$) comparison for both viscosities of water and 3 cP glycerol solution as a function of angle.

It should be understood that in accordance with the present teachings, both the surface feature 30 size and shape (e.g. 3-50 µm, sinusoidal or directional) will have an impact when tuning for different, non-Newtonian viscosities. According to our data, we have seen that surface tuning has greater effects on higher viscosity fluids, e.g. water versus glycerol, as can be seen in FIGS. 5A-5D. That is, as seen in FIGS. 5A-5D, pump pressure over time with a 0 degree print (FIG. 5A) can be compared to pump pressure over time with a 22 degree print (FIG. 5B) and a 45 degree print (FIG. 5C). Likewise, the final hydrostatic pressure ($\rho g \Delta h$) comparison for both viscosities of water versus glycerol as a function of angle, with 45 degree maxing out around 630 Pa. Higher viscosity 3 cP glycerol solution saw a larger increase in pumping pressure due to rotor surface geometry.

In addition, non-Newtonian fluids, such as shear-thinning blood, have greater shear gradients near the walls as explained earlier. Therefore, blood may get thinner near the walls, requiring a larger surface feature size to provide the same coupling improvements than Newtonian fluids of the same viscosity.

Although additional benefits may be realized, it should be noted that two particular aspects of the µTesla pump 10 make it well-suited for biofluidic pumping. First, the rotor assembly 14 is designed to be magnetically coupled to external electromagnets 32 and can be completely isolated in microfluidics. The seal-free design eliminates leakage problems and external contamination sources, and lowers the cost of pump assemblies due to its replaceable rotor assembly 14. Second, the µTesla rotor assembly 14 consists of only circular disks 12—here 3D printed but can be potentially molded—connected by a simple spindle structure 34. Under fluid flow, the rotor assembly 14 will be self-aligned due to hydrodynamic forces and its magnetic coupling. The simplicity of the surface-fluid coupling eliminates and prevents stress concentrations exerted anywhere on the rotor assembly 14 itself, increasing the reliability and reducing the chance of failure during operation. Should failure occur, the rotor assembly 14 is devoid of small blade-like structures that can potentially be dragged into the fluid. Instead, any fragments of disks 12 of µTesla motor 10 would be trapped by the housing 36 in the pump assembly, which makes it safe for potential embedded clinical application.

3D Printing for Microstructured µTesla Fabrication

Figures 6A, 6B:
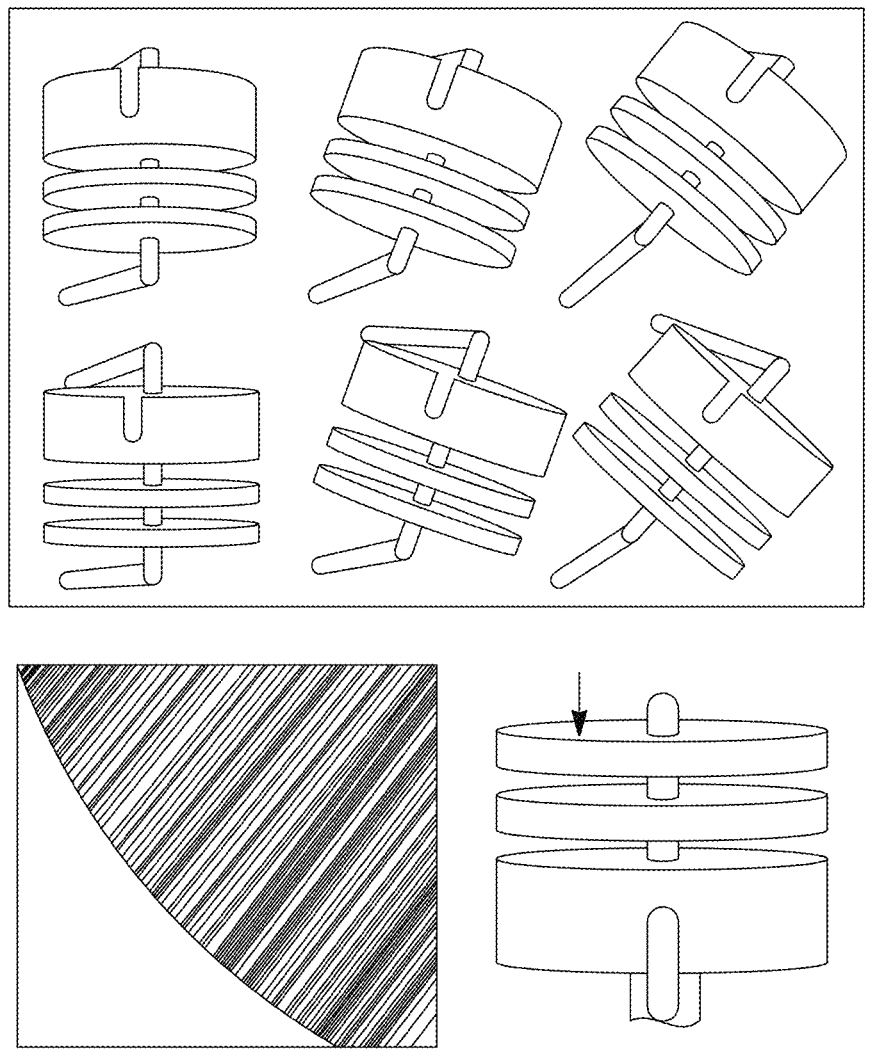
FIG. 6A illustrates side views of 3D printing to create pixelation for surface topology.
FIG. 6B illustrates increased topology as print angle varied up to 45°.

In some embodiments, µTesla motor 10 can be fabricated using a digital light processor (DLP) based 3D printer with x-y-z resolution of 50 µm. Using a novel technique, the surface topology was tuned via "3D pixelations" by printing the disks 12 at an angle to the axes of a 3D stereolithography printer, as illustrated in FIG. 6A. When edges of the disks 12 are printed in parallel with the axis of the 3D printer, the pixels form a line with no deviations. As the angle between the disk 12 print and the 3D printer axis is increased, the edge becomes jagged, with maximum pixelation at 45°. This "pixelation" can occur in all three dimensions since the printing technically forms a 3D voxel. Using this technique, the surface topology was varied between 0, 22, and 45°, but it should be understood that additional topology configurations, shaped, and angles are anticipated.

Additionally, it should be noted that 3D printing could also arbitrarily describe surface topologies beyond 3D pixelations. Due to the directional rotation of the μTesla rotor assembly 14, directional topology, e.g. triangles, arrow heads, can be designed using high resolution 3D printing.

3D Printed Rotor Surface Topologies

Using a digital light projector (DLP) based 3D printer, the print of the disks 12 was rotated at 0°, 22.5°, and 45° with respect to the axis of the 3D printer. Disks of all three print angles could be printed simultaneously to speed up prototyping, but elicit controlled variations of surface topologies along the edges of the rotors. The layers are created tangentially to the circumference of the disk and continue throughout the rotor in that manner. We used a surface profilometer to characterize the topology using the RMS (root-mean-square) of the height deviations at each rotor surface. As expected, the 45° print incurred the greatest surface topology at 3.30 μm, followed by 22.5° at 3.13 μm. The non-rotated, 0° print was measured at 3.01 μm representing the base surface roughness of aligned voxels.

This information is shown in FIG. 6B. It presents a clear positive trend associating rotor angle to surface topology. Moreover, the observed differences in surface topology yielded measurable differences in rotor response and flow characteristics.

μTesla Hydraulic Head Versus Surface Topology

Figure 6C:
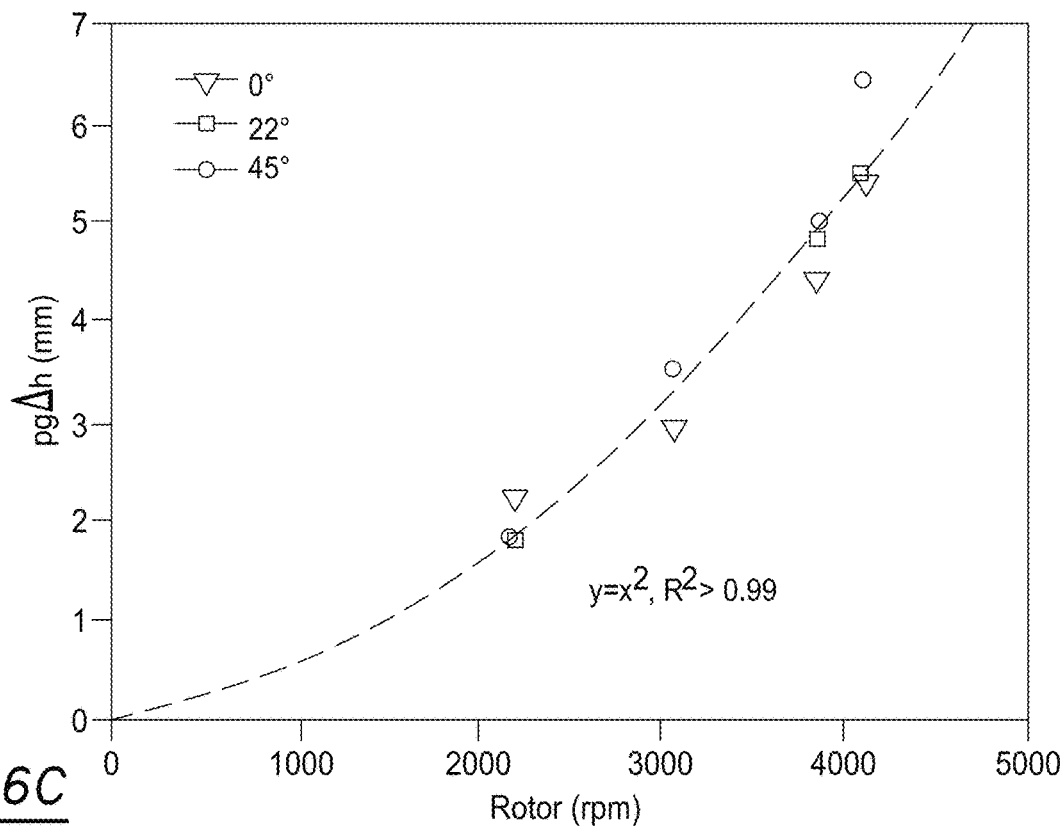
FIG. 6C illustrates a graph of $\rho g \Delta h$ pressure over rotor speed (rpm) with a 45° printed rotor.
Figure 6D:
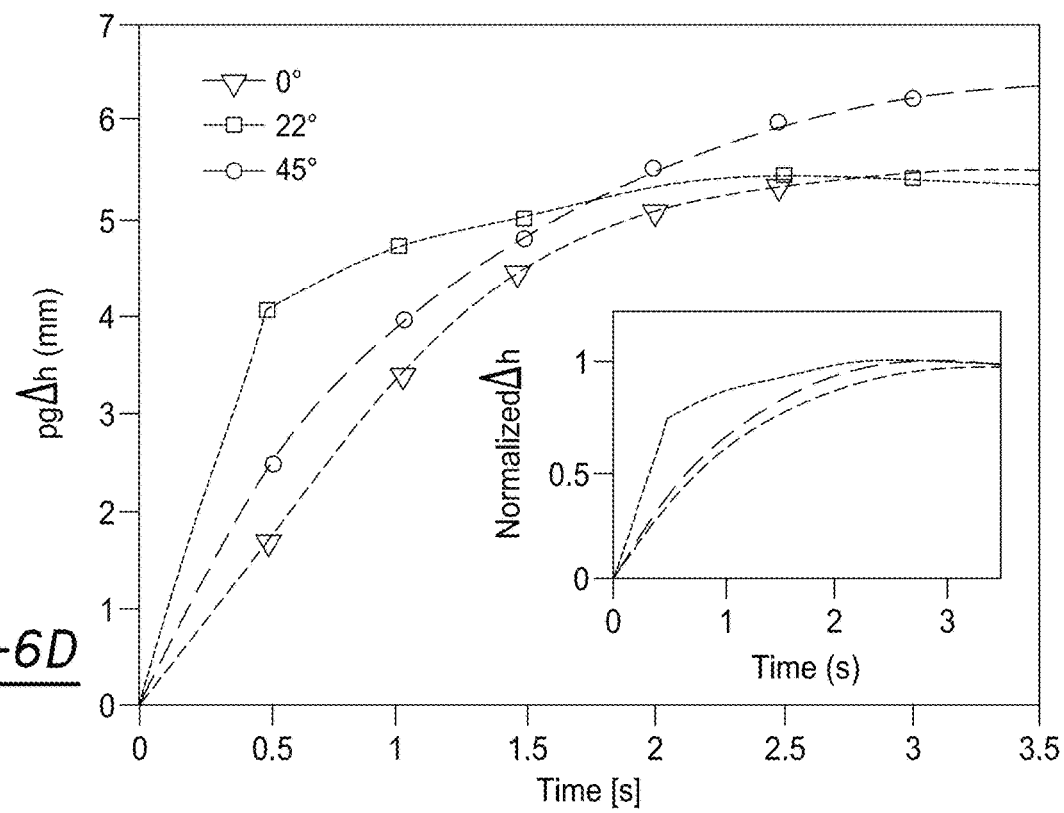
FIG. 6D illustrates a graph of $\rho g \Delta h$ pressure over time.
Figure 7C:
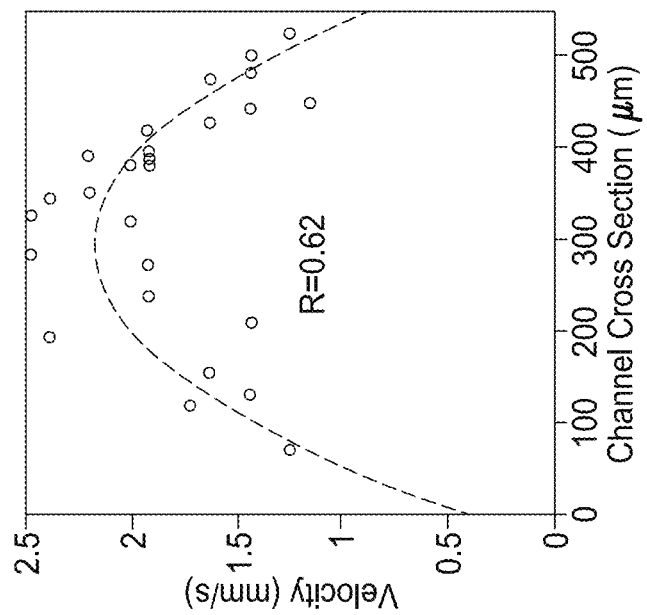
FIG. 7C illustrates a graph showing that the peristaltic pump incurred pressure, and thus velocity, fluctuations that degraded its laminar flow profile.
Figure 7B:
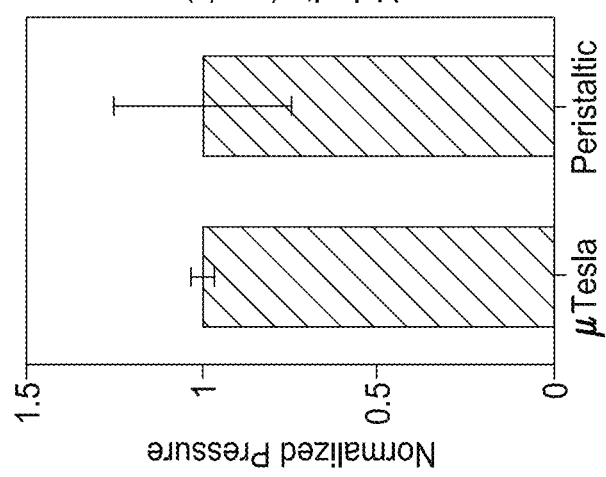
FIG. 7B illustrates a graph showing pressure variation was less than 5% in the µTesla pump versus over 25% in peristaltic pump at 30 µL/min.
Figure 7A:
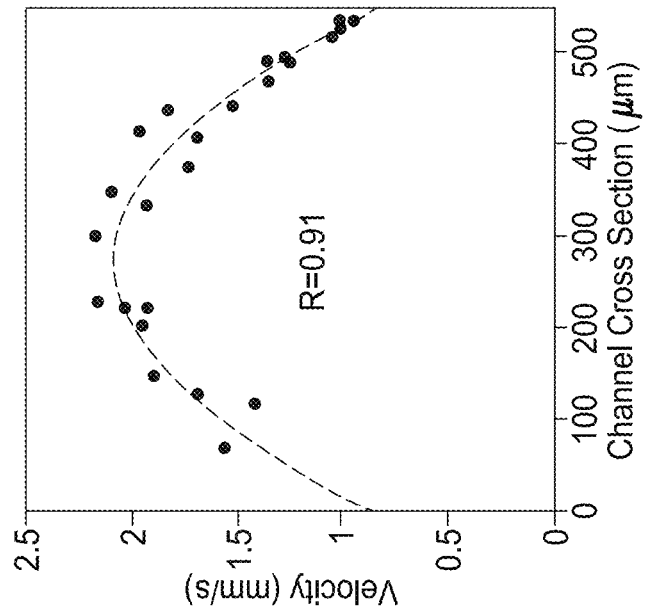
FIG. 7A illustrates a graph showing that the µTesla motor of the present teachings generated flows that closely follow the parabolic profile of laminar flow.
Figure 8A:
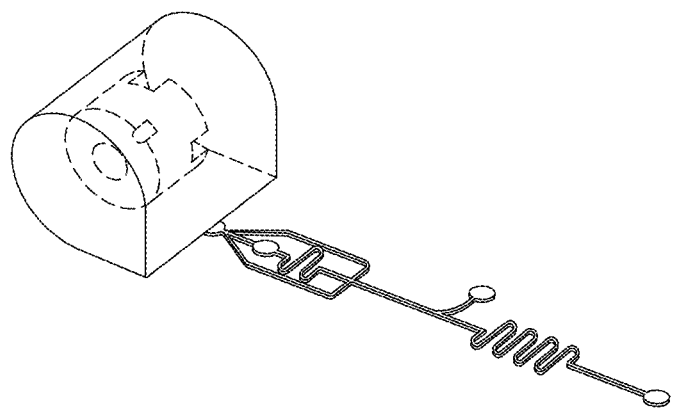
FIG. 8 illustrates perspective views of the µTesla pump according to the principles of the present teachings.
Figure 8B:
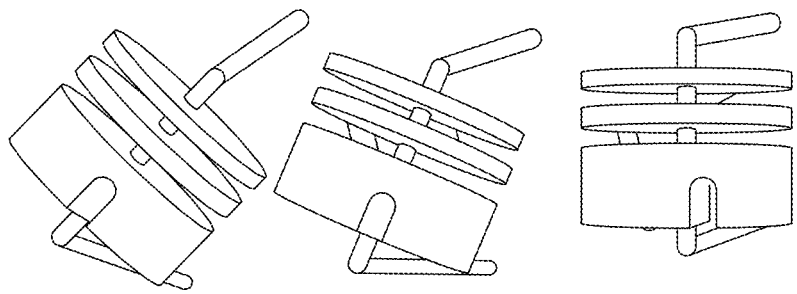
Figure 8C:
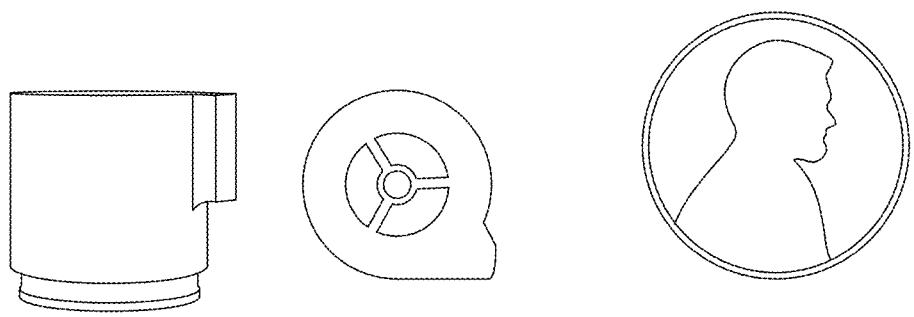
Figure 8D:
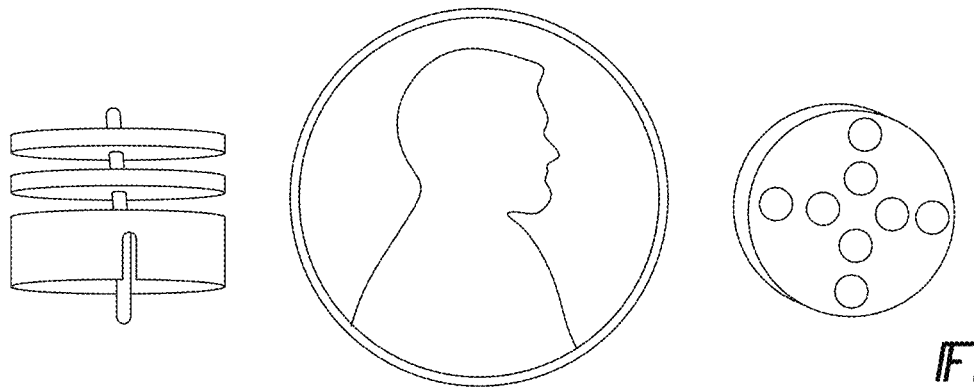

Moreover, the rotor assembly and disks were applied to pump water, and the unloaded hydraulic pressure ρgΔh versus rotor speeds were characterized, see FIG. 6C. To measure the rotor speed, the rotors were painted with a silver ink spot and read by an optical tachometer during operation. Maximum pressures were acquired and compared in FIG. 6C. The measurements showed that the increased surface topologies of the 22.5° and 45° printed rotors lead to higher pump outputs than the 0° printed rotor.

μTesla Transient Characteristics

Additionally, the rotor assembly and disk response were improved by surface topology. To quantify this, slow motion video at 120 frames per second (fps) was acquired to image both ρgΔh and tachometer speeds over time. Our results showed both 0° and 45° rotors took more than 2 seconds to reach maximum pressure, while 22.5° rotor reached a stable rotor speed after 1 second, see FIG. 6D. The different maximum pumping output and transient times could determine the most suitable application for each rotor. The 0° rotor would be most suitable for applications requiring a larger transient time, whereas a 22.5° rotor would be most suitable for an application requiring a smaller transient time. In addition, the 0° rotor could be used to pump larger volumes, whereas the 22.5° and 45° rotors could be used to pump smaller volumes.

μTesla Provides Accurate Shear Modulations

To illustrate the differences between pulsatile and non-pulsatile flows, two closed-loop microfluidics were constructed using a peristaltic pump vs. μTesla pump 10 (without surface topology). Then, gold nanoparticles (GNP, 50 nm diameter) were injected into the closed loop system to image the flow rates using particle velocimetry. Under dark field illumination and a camera integration time of 100 ms, particle streaking was imaged and calibrated to give the particle velocity at various cross sectional positions. The velocity profile of the μTesla pump 10 flow renders the familiar parabolic shape for laminar flows, $R^2=0.91$, see FIG. 7A, with pressure variations less than 5% over 5 minutes of pumping. On the other hand, the peristaltic pump showed pressure fluctuations over 25% with time, see FIG. 7B. Moreover, its velocity profile yielded a poor fit of $R^2=0.62$, see FIG. 7C. This is more due to the peristaltic nature of the flow, as often times the velocity stopped and reversed, which lead to a spread of the data points. Considering the effects in a blood vessel, a 25% change of velocity will lead to a 25% change of the exerted shear stress. This has implications in modeling normal versus pathological shear, e.g. 17 mPa versus 21 mPa in diabetic islet microvasculatures. This means that if one targets physiological shear ranges of 17 mPa, 25% error from peristaltic pump will generate fluctuations that extend into pathological ranges of 21 mPa, while the μTesla pump 10 will remain under 18 mPa. These results show that μTesla pump 10, even without surface topology optimization, is more suitable for modeling shear flow.

The combination of stability, precision, and low cost makes the μTesla pump 10 an exceptional flow source for microfluidics. As shown, the 45° print produced a steady pressure greater than 630 Pa. This demonstrates that the rougher the topology of the rotor, the higher the ability to push flow through the pump. With the understanding of how surface roughness can impact pump output of solutions with different viscosities, print angles and 3D pixelation can be tuned for specific biological viscosities.

It should be generally understood that the effects of surface structuring on pump pressure will be greater for non-Newtonian fluids with viscosities greater than 3 cP compared to Newtonian fluids like water. Generally, the surface structures should have vertical and lateral features on the scale of 3-50 μm. Any features smaller than this will have surface roughness effects that change how the fluid contacts the solid material. Any features larger than this will have effects on bulk fluid and produce unwanted pressure waves.

The surface structure can be symmetrical, e.g. an equilateral triangle, or directional, e.g. a saw tooth shape. Directional structure, e.g. saw tooth, will have greater effects on pumping in one rotor direction than the counter direction. The surface structure can be a smooth sinusoid. This is based on the concept of single harmonic frequency being applied to reduce extraneous fluctuations. For the same vertical and lateral size scales, the sinusoid structure should have smaller pressure fluctuations while maintain the same fluid-surface coupling. The surface structure can be a rectangular profile, which can provide the maximum coupling at 50-50% duty cycle. Lower duty cycle rectangular profiles will improve fluidic coupling and pump pressure, at the expense of more pressure fluctuations. Higher duty cycle will lower fluctuations at the expense of maximum pump pressure.

μTesla Pumping of Non-Newtonian Fluids

Figure 9:
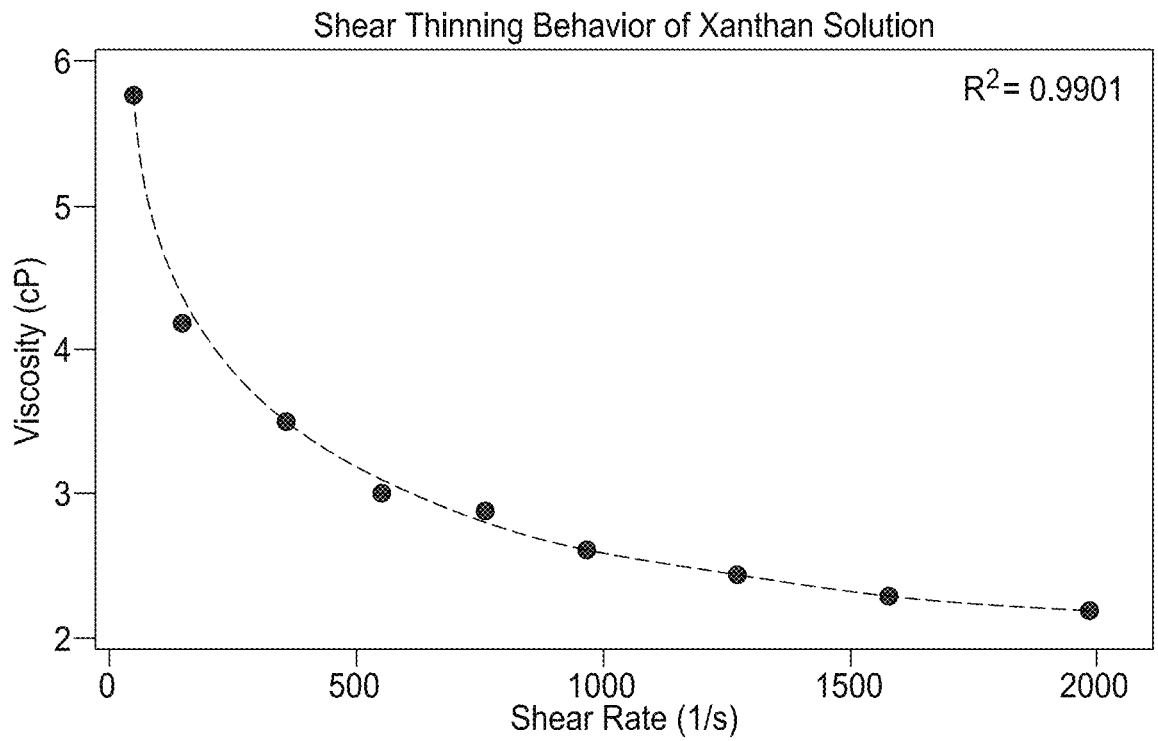
FIG. 9 illustrates shear thinning behavior of Xanthan solution to model blood.

Non-Newtonian fluids have rate dependent viscosity. For biological fluids, the viscosity is shear thinning and decreases with increasing shear rate, making the fluid easier to pump. To investigate μTesla tuning for shear thinning fluids according to the principles of the present teachings, a blood analogue fluid was prepared with Xanthan gum in water, FIG. 9. At higher physiological shear rates, e.g. 1000 $s^{-1}$, the Xanthan solution approaches the nominal 3 cP associated with blood.

Figure 10A:
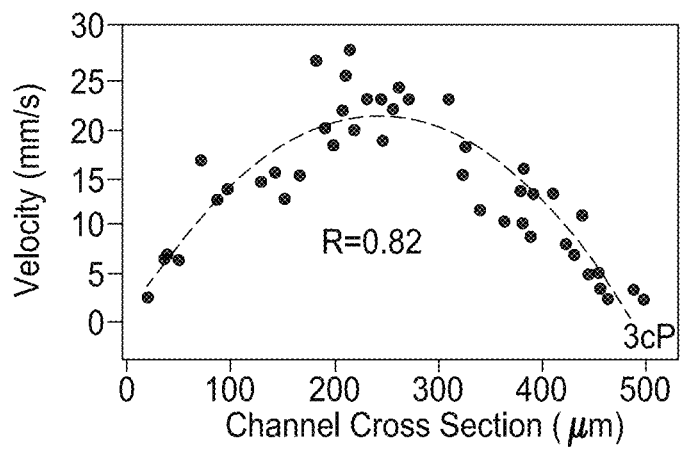
FIG. 10A illustrates the velocity profile of glycerol solution (3 cP) driven by µTesla in 500 µm channel.
Figure 10B:
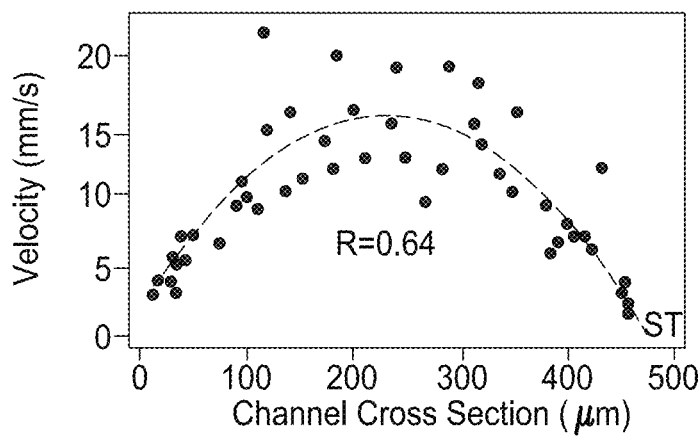
FIG. 10B illustrates the velocity profile of Xanthan solution (shear thinning) driven by µTesla.

While Newtonian fluids have parabolic velocity profiles, FIG. 10A, shear thinning deviates from the parabola with a flatter velocity profile, FIG. 3, FIG. 10B. This suggest that the tuning of μTesla surface texture for shear thinning biological fluids must be distinct from simple Newtonian fluids, even at the same viscosity ranges.

Distinct μTesla Tuning for Shear Thinning Fluids

This fluid was then pumped with the three textured μTesla rotors at 0, 22, and 45° print angles, with their output pressures quantified, FIG. 11. Results show that optimal surface texture can be tuned for Xanthan solution in the same manner as 1 cP water and 3 cP glycerol. For all three solutions, the 22° rotor yielded the highest output pressure, FIG. 11D-F. As only three rotor angles were tested, increasing the gradation of surface textures beyond these angles will reveal the actual optimal point for each fluids.

Furthermore, while increasing the Newtonian viscosity from 1 cP to 3 cP yielded higher output pressures for all rotor angles, the Xanthan solution (despite being nominally 3 cP) exhibited a break from this trend at the 22° rotor angle. At the 22° rotor angle, the Xanthan fluid is better coupled to the μTesla rotor surface. This enhanced coupling presents a larger shear gradient and stress across the Xanthan solution, decreasing its overall viscosity via shear thinning. This explains the seemingly contradictory, yet fluid mechanically justified, drop in output pressure. The overall effect is that Non-Newtonian tuning of μTesla pumping changes the fluid-surface boundary significantly. The inherently different velocity profiles, FIG. 3, FIG. 10B, together with the Xanthan result at 22° rotor angle supports the claim that there should be distinct tuning points for different viscosities and Newtonian vs. non-Newtonian fluids.

Boundary Layer Effects of μTesla Tuning

According to the present teachings, it should be understood that the boundary layer between the fluid and μTesla rotor surface is modified by the added surface textures, in a manner that increases the coupling and extends the boundary layer effects. Normal boundary layer flow is depicted in FIG. 12A. When the non-zero slip velocity $U_S$ is projected beyond the y-axis, a mathematical slip distance $\lambda_s$ can be quantified, whose sign is positive towards the left by convention. When texture is added to the surface, the velocity profile is pushed towards the right side, FIG. 12B. The effect on the projected $U_S$ is a reduction of $\lambda_s$ towards the right side. In the extreme example shown here, the resultant slip distance can become negative in sign by convention. Physically, this reduction of slip distance in effect makes the fluid stickier to the surface.

In contrast, several contemporary techniques alter the fluid-surface boundary by adding nanotextures that are hydrophobic, FIG. 12C. This, in essence, traps air pockets in the alternative grooves of the boundary walls, reducing the averaged solid surface in contact with the fluid. The physical result is an increase in slip distance, making the fluid slipperier and easier to flow.

To investigate the claimed slip boundary manipulation, in silico model of the fluid dynamics was constructed in finite element software and solved, FIG. 13. The result showed that surface texture indeed modifies the velocity profile, pushing the slip velocity further out towards the center of the fluid flow (to the right), FIG. 13B-D. By injecting additional fluid properties and measuring μTesla pump pressures to detail mechanics and characteristic slip length, $\lambda_s$ can be calculated for any combination of surface texture and fluid viscosities.

Accordingly, it should be understood that the μTesla pump and its associated surface optimization techniques and features of the present teachings apply to non-Newtonian fluids (as demonstrated by shear-thinning Xanthan). Moreover, general trends of optimization are the same (medium texture works best), but specific output pressures from Xanthan suggest that different optimal points exists for non-Newtonian vs. Newtonian fluids. Finally, the scale of the described surface textures theoretically reduces the slip distance that characterizes the fluid-surface interface. The ability to manipulate the slip distance is corroborated by what has been shown in aerodynamics, although for the opposite effect of more slip in those cases.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A miniaturized, magnetically-coupled Tesla pump for pumping variable viscosity fluid, the miniaturized, magnetically-coupled Tesla pump comprising:
   a housing having an axial input and a lateral output;
   a rotor assembly having a plurality of disks rotatably supporting within the housing, each of the plurality of disks having a surface and defining a space between adjacent disks, the rotor assembly having an axial spindle extending between the plurality of disks, the rotor assembly configured to generate a non-oscillatory pressure to pump the fluid from the axial input to the lateral output; and
   a plurality of microstructures extending from the surface of at least one of the plurality of disks to define a surface topology extending between the plurality of disks, each of the plurality of microstructures configured to generate fluid-surface coupling without perturbing laminar flow profile, each of the plurality of microstructures has a periodic spacing in the range of 3 to 50 μm.

2. The miniaturized, magnetically-coupled Tesla pump according to claim 1 wherein each of the plurality of microstructures being between 100 nm and 100 μm in height.

3. The miniaturized, magnetically-coupled Tesla pump according to claim 1 wherein each of the plurality of microstructures being between 3 and 50 μm in height.

4. The miniaturized, magnetically-coupled Tesla pump according to claim 1 wherein each of the plurality of microstructures are symmetrical.

5. The miniaturized, magnetically-coupled Tesla pump according to claim 1 wherein each of the plurality of microstructures are triangles.

6. The miniaturized, magnetically-coupled Tesla pump according to claim 1 wherein each of the plurality of microstructures are equilateral triangles.

7. The miniaturized, magnetically-coupled Tesla pump according to claim 1 wherein at least one of the plurality of microstructures is different than another of the plurality of microstructures.

8. The miniaturized, magnetically-coupled Tesla pump according to claim 1 wherein each of the plurality of microstructures is directionally shaped to provide increased fluid-surface coupling in a first direction and decreased fluid-surface coupling in a second direction.

9. The miniaturized, magnetically-coupled Tesla pump according to claim 1 wherein each of the plurality of microstructures are sinusoidal.

10. The miniaturized, magnetically-coupled Tesla pump according to claim 1 wherein each of the plurality of microstructures are rectangular.

11. The miniaturized, magnetically-coupled Tesla pump according to claim 1 wherein each of the plurality of microstructures defines an angle less than about 45 degrees.

12. The miniaturized, magnetically-coupled Tesla pump according to claim 1 further comprising:
   a magnetic drive system magnetically coupling with the rotor assembly to rotate the rotor assembly relative to the housing.

* * * * *